United States Patent
Beard et al.

(10) Patent No.: US 6,204,669 B1
(45) Date of Patent: *Mar. 20, 2001

(54) DETECTION OF DEFECTS IN PROTECTIVE BARRIERS

(75) Inventors: Richard B. Beard, Atco, NJ (US); Kambiz Pourrezaei, Dresher, PA (US); Shengke Zeng, Morgantown, WV (US); Frederick Prout, Huntington Valley, PA (US); Frank M. Kepics, Eagleville, PA (US); Jin Park, Exton, PA (US); Allen Rothwarf, deceased, late of Philadelphia, PA (US), by Bernice Rothwarf, legal representative; Siddharth Deliwala, Morrisville, PA (US); Robert Schmukler, Rockville, MD (US)

(73) Assignee: Drexel University, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/109,882

(22) Filed: Jul. 2, 1998

Related U.S. Application Data

(60) Provisional application No. 60/051,585, filed on Jul. 2, 1997.

(51) Int. Cl.[7] .................................................. G01N 27/00
(52) U.S. Cl. ............................................................ 324/557
(58) Field of Search .................................... 324/557, 558, 324/551, 559

(56) References Cited

U.S. PATENT DOCUMENTS

| | | |
|---|---|---|
| 4,583,039 * | 4/1986 | Kolcio et al. ........................ 324/54 |
| 4,810,971 | 3/1989 | Marable . |
| 4,956,635 | 9/1990 | Langdon . |
| 5,059,913 | 10/1991 | Nigro et al. . |
| 5,097,214 * | 3/1992 | Schinharl ............................ 324/554 |
| 5,114,425 | 5/1992 | Williams et al. . |
| 5,129,256 | 7/1992 | McGlothlin . |
| 5,196,799 | 3/1993 | Beard et al. . |
| 5,204,632 | 4/1993 | Leach . |
| 5,351,008 | 9/1994 | Leach et al. . |
| 5,389,097 | 2/1995 | Bennett et al. . |
| 5,448,177 | 9/1995 | Thompson . |
| 5,455,507 | 10/1995 | Horenstein . |
| 5,493,899 | 2/1996 | Beck et al. . |
| 5,524,478 | 6/1996 | Joy et al. . |
| 5,600,250 | 2/1997 | Thompson . |
| 5,963,040 * | 10/1999 | Liu ....................................... 324/551 |

OTHER PUBLICATIONS

J.K. Bennett, "Safety and Reliability of Latex Surgical Gloves", no date, 2 pages.
D.M. Korniewicz et al., "Barrier Integrity of Gloves Used in Clinical Practice", (1995 or 1996), 3 pages.
Ansell Healthcare Division—Home Page: "The Electronic Testing of Gloves"; "Testing Gloves for Holes"; "Surgical Gloves: Double–Gloving and Perforations" and attachments (1995 or 1996), 12 pages.
ECI Medical Technologies Inc.—Web Page for Elastyren, 6 pages (1996).

* cited by examiner

*Primary Examiner*—Safet Metjahic
*Assistant Examiner*—J Kerveros
(74) *Attorney, Agent, or Firm*—Akin, Gump, Strauss, Hauer & Feld, L.L.P.

(57) ABSTRACT

The invention includes apparatus and method for detecting defects in various barrier materials including surgical gloves and food packaging. Voltage is applied across electrodes and a barrier material and the voltage measured and compared with voltage control measurements for the same barrier material without a defect. Sensitivity of measurements is increased by adjusting partial pressure across the barrier material which is subjected to the passage of an ionized gas detected by suitable instrumentation.

20 Claims, 6 Drawing Sheets

———— Positive Ion Density Distribution
------- Negative Ion Density Distribution ———— Positive Ion Density Distribution
------- Negative Ion Density Distribution FIG. 5
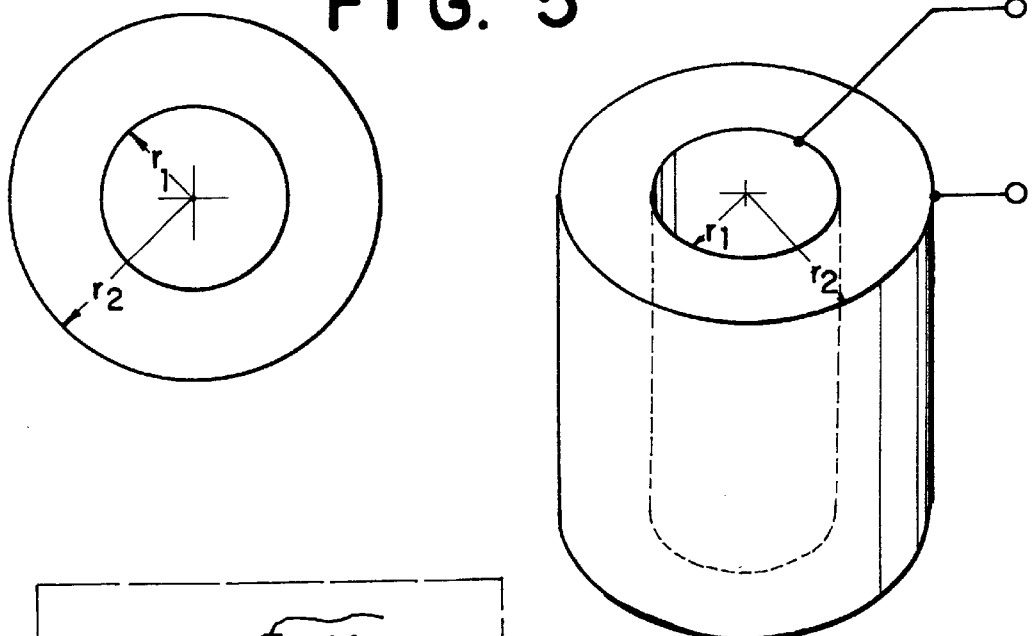
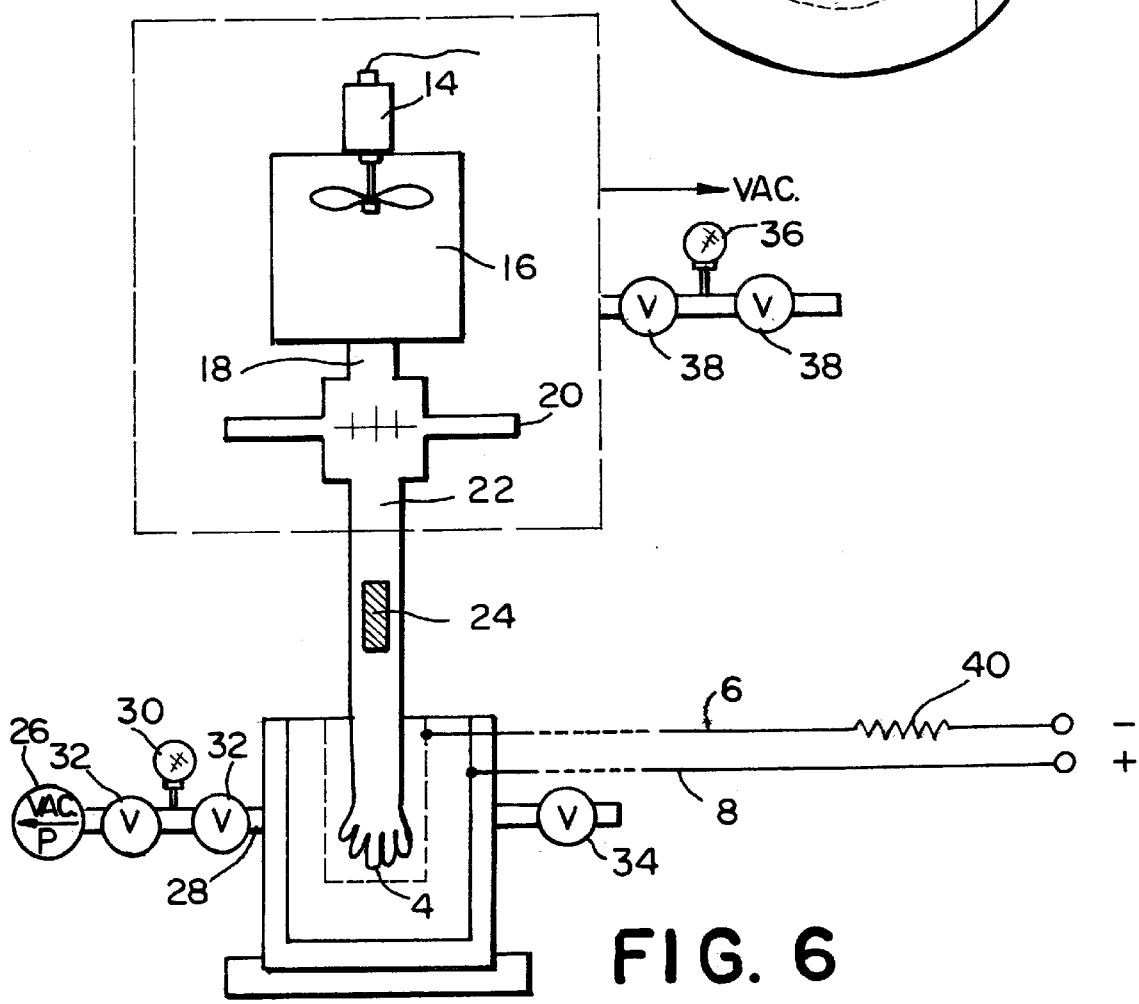
FIG. 6

DETECTION OF DEFECTS IN PROTECTIVE BARRIERS

CROSS REFERENCE TO RELATED APPLICATION

This application claims the benefit of United States Provisional Application No. 60/051,585, filed Jul. 2, 1997, entitled "Detection of Defects in Barriers, the entire disclosure of which is incorporated herein by reference."

BACKGROUND OF THE INVENTION

There is a great concern among world health organizations and regulatory agencies as to the quality of protective products such as condoms, gloves, implantable enclosures (breast implants), protective garments, and medical and food packaging to ensure protection against sexually transmitted diseases and toxic materials. The greatest concern in health care and toxic industrial environments is that these products be free from defects before and during usage. Protective barriers come in a wide variety of geometries, thicknesses and materials of construction depending upon the application. Latex and synthetic polymers are frequently used for barriers such as condoms, gloves, garments and implants. Although packaging may be formed only of polymeric material, it may also include other types of materials to ensure the integrity of the packaging, such as metallic films. Other composite materials may be used in other areas of applications as barrier materials, for example, in a work place involving electrical and/or chemical hazards.

Defects such as holes and tears can occur in a variety of geometries and sizes, from large tears to small pinholes. In health care applications in order to protect health care providers, the acceptable defects are preferably in the micron or sub micron range. The herpes virus is about 0.15 micron, and the AIDS virus, about 0.1 micron. Small biological particles may be charged, producing ionic layers about the particle which hydrodynamically create much larger particles. However, even with a considerably larger particle size, such biological particles will be in the micron range.

In industrial applications protective clothing must present a barrier to hazardous chemicals in various states, e.g., liquid, gaseous and vapor states. Important parameters in such applications include breakthrough times and permeation rates as measured for various chemicals and barrier materials. S.P. Beradinelli et al., *am. Ind. Hyg. Assoc. J.* 48 (9), pp. 804–808 (1987); J.O. Stull et al., *Am. Ind. Hyg. Assoc. J.* 51 (5), pp. 291–296 (1990).

Variation in experimental data in testing barrier materials are believed to be caused by specimen variations rather than variations in the test system. Test specimens are not in many cases inspected for small defects such as pin holes S.P. Beradinelli et al., *Am. Ind. Hyg. Assoc. J* 51 (11), pp. 595–600 (1990). Thus variations in testing can be caused by defects as well as variations in the material thickness and compositions. Beradinelli et al., *Am. Ind. Hyg. Assoc, J.* 46 (2), pp. 60–64 (1985); J.F. Stanpfers et al., *Am. Ind. Hyg. Assoc. J.*, 45 (9), pp. 642–654 (1984); S. Zing et al., *J. Clinical Eng.* 21 (6), pp. 456–465 (1996). The monitoring of defects as well as permeation of hazardous chemicals through protective barriers is essential for safety in the work place.

Estimates have been given that at least 2 million people annually are exposed to a variety of hazardous liquid chemicals. D.A. Jenien et al., *Am. Ind. Hyg. Assoc. J.* 49 (6), pp. 293–300 (1988); National Institute for Occupational Safety and Health, DHEW/NIOSH Pub. No. 74–137 U.S. Gov. Doc. Printing Office, p. 22 (1974); National Institute for Occupational Safety and Health, DHEW/NIOSH Pub. No. 749–106, Cambridge, Mass. A.D. Little, pp. 210–260 (1979). Chemical gases and vapors are routinely encountered in a number of different industries where workers must be protected by clothing impermeable to gases. Reports from three surveillance systems demonstrate 587 acute releases of hazardous materials in 1986, which resulted in 115 deaths, 2,254 injuries and 111 evacuations S. Binder et al., "Acute Hazardous Materials Release," *Am. J. of Public Health,* vol. 79, No. 12, pp. 1681 (Dec. 1989); S. Binder, *Am. J. Public Health,* Vol. 79, No. 8, pp. 1042–1044 (Aug. 1989). Even with limited information, five states reported to the Hazardous Substances Emergency Events Surveillance (HSEES) system that for 2,391 fixed-facility events and 723 transportation-related events, 1,446 persons were injured and 11 persons killed. MMWR, CDC Surveillance Summaries, vol. 43, No. 55-2 (Jul. 22, 1994). The most frequently released hazardous substances were volatile organic compounds, herbicides, acids and ammonia Workers involved in hazardous waste disposal have the need to be protected from a range of toxic liquids, gases and vapors. In the health care industries, inspection gloves and, in particular, surgical gloves are required to protect people from a variety of pathogenic agents. In all of the above applications, it is desirable that protective barriers be free of defects which compromise the integrity of the barrier. As such, there is a need in the art to ensure the integrity of protective barriers for the safety of well over 2 million people annually.

The evaluation of the integrity of protective clothing for industrial and medical applications has involved batch testing by electrical methods as in S. Zing et al. *J. Clinical Eng.* 21 (6), pp. 456–465 (1996) and permeation as in, for example, R. Mickelsen et al., *Am. Ind. Hyg. Assoc. J.* 48 (11), pp. 941–947 (1987).

Due to potential defects during manufacturing, techniques are needed to evaluate each protective barrier on an inspection line following a manufacturing process. Some products such as condoms have a geometry which makes feasible the testing of each condom on a conductive mandrel. Condoms over a conductive mandrel placed in a conductive bath using a Q meter are described in U.S. Pat. No. 5,196,799 have been monitored for micron defects on an inspection line. Gloves have a geometry which makes impractical the testing of each glove on an inspection line using a mandrel unless a conductive mandrel is used to form the glove in the dipping process. Surgical gloves have the problem of sterilization during and after inspection. In many cases such a technique using conductive sterile baths would not be acceptable.

In chemical protective clothing (CPC), the resistance to permeation is essential to the integrity of the protective barrier. One measurement of the resistance to permeation is the breakthrough time defined as the elapsed time between initial contact of the hazardous liquid chemical with the outside surface of a protective barrier and the time at which the chemical can be detected at the inside of the barrier material. R.L. Mickelsen et al., *Am. Ind. Hyg. Assoc. J.* 48 (11), pp. 941–947 (1987). The steady state permeation rate is another measurement used in evaluating the integrity of CPC. J.F. Stanpfers et al., *Am. Ind. Hyg. Assoc. J.,* 45 (9), pp. 642–654 (1984). Permeation in barrier materials is considered to be a molecular process by which a chemical moves through a material. The process involves (i) adsorption of the chemical liquid, vapor or gas onto the material surface;

(ii) difffusion through the material; and (iii) absorption from the opposite side of the material. S. Binder, *Am. J. Public Health,* vol. 79, No. 8, pp. 1042–1044 (Aug. 1989); National Institute for Occupational Safety and Health, DHEW/ NIOSH Pub. No. 74–137, U.S. Gov. Doc. Printing Office, p. 22 (1974).

There have been some new approaches which attempt to overcome difficulties associated with geometry, sterilization, and various barrier materials. Stampfer et al. working with NIOSH have developed a technique for laboratory glove testing using a conductive fluid as a mandrel by filling the glove with a conductive saline solution and then placing the glove in a conductive bath. A major difficulty with this approach is there is high conductivity associated with many barriers fabricated of synthetic polymers which are very conductive, thereby making electrical measurements very insensitive.

As such, there is still a need in the art for an improved method for testing glove and other barrier materials for defects which is reliable and reproducible.

DETAILED DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, like numerals are used to indicate like elements throughout. In the drawings:

FIG. 5 is a schematic representation of the radii of concentric screens in the apparatus of FIG. 4;

FIG. 6 is a schematic representation of a system for testing barrier materials in accordance with a further embodiment of the invention with a portion of the apparatus broken away;

BRIEF SUMMARY OF THE INVENTION

Figure 1:
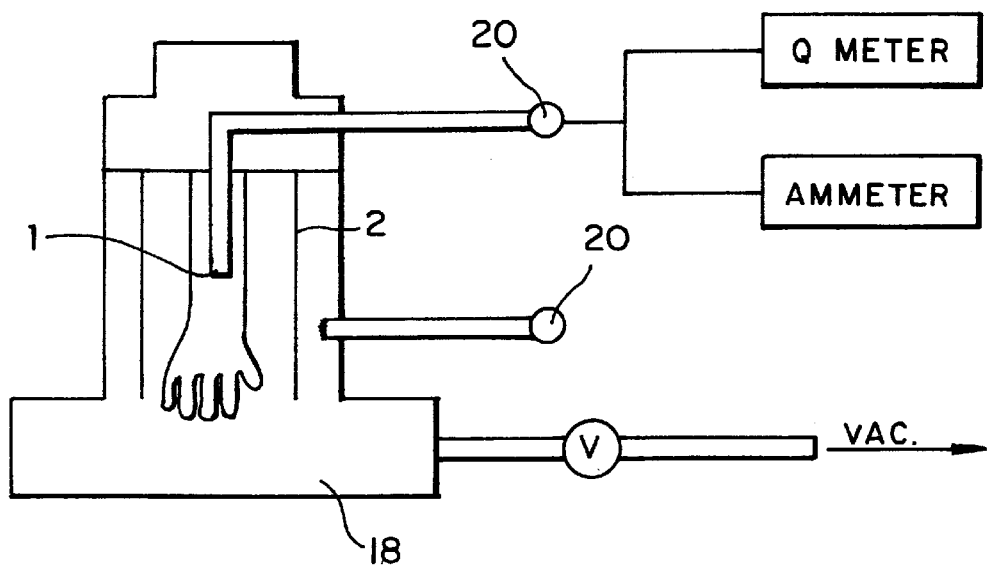
FIG. 1 is a schematic representation of an apparatus in accordance with the invention.

The invention includes an apparatus for detecting defects in a barrier, comprising
 (a) a barrier formed from a barrier material subjected to voltage from a voltage source across a first electrode and a second electrode;
 (b) an ionizer;
 (c) a gas inlet for introducing a gas to be ionized;
 (d) a vacuum source for drawing a gas to be ionized through an ionizer and through the barrier,
 (e) a controller for controlling a pressure differential across the barrier; and
 (f) a determination source for comparing electrical output for background permeation of ionized gas through the barrier material when the barrier material is free of defects with the output of ionized gas through the barrier.

The invention further includes a method for detecting defects in a barrier formed from a barrier material, comprising applying a voltage across a first electrode and a second electrode and across said barrier, subjecting said barrier to an ionized media; drawing the ionized media through the barrier, measuring the voltage across the barrier when the ionized media is drawn through the barrier; and comparing the voltage across the barrier to a voltage measured across a defect free barrier formed of the barrier material.

The invention also includes an enclosure apparatus for testing surgical gloves, comprising at least one chamber; an inlet for introducing a surgical glove; a gas inlet for passing gas through a surgical glove; a screen for constraining the glove; a vacuum source for drawing gas through a surgical glove; an ionizing source; and a detector for monitoring voltage across a surgical glove within the screen.

DETAILED DESCRIPTION OF THE INVENTION

The following is a detailed description of the preferred embodiments of the invention and should not be construed as limiting the scope of the applicants' invention. Applicants have discovered that by placing a conductive liquid on one side of a protective barrier and an ionized gas on the other side, a method for testing the material which is reliable and practical is achieved.

This disclosure will first concentrate on methods for monitoring defects in gloves using nitrogen, as described further below, and then discuss methods for preventing hazards caused by glove permeation of toxic gases such as encountered in semiconductor processing mixtures.

This invention provides new approaches based on ionized gases as conductive media which is useful in various applications including complex geometries, very conductive barrier materials, and products requiring sterilization.

In the approach presented in this disclosure using conductive ionized gas as a sterile fluid, defects in gloves and protective clothing can be monitored on inspection lines and in laboratory measuring enclosures. This permits monitoring of the protective barriers on the parts which exhibit the greatest likelihood for defects. S.P. Beradinelli et al., *Am. Ind. Hyg. Assoc. J.* 48 ( 11) pp. 941–947 (1987).

The object of this invention is to provide a monitoring technique for defects and for permeation of protective barriers for application to inspection lines as well as laboratory measurements and to thereby ensure the integrity of manufactured barriers to hazardous chemicals and/or transmitted diseases.

Conductive ionized gas particles pass through a defect to be sensed and cause a change in conductivity of the liquid as measured by an electrode placed in the conductive liquid. For example, physiological saline is placed inside condoms and gloves which are then exposed to a flow of ionized gases such as air and pure nitrogen. Because of the detrimental influence of ozone, air would not be used on rubber latex gloves or condoms. Other gases such as nitrogen which are not detrimental could be used. The Q meter described in U.S. Pat. No. 5,196,799, which is incorporated by reference herein, can be used as a detector of such defects by placing it across the outer electrodes 1 and inner electrodes 2, as shown in FIG. 1. If a programmable voltage source is used with an ammeter, the current can be measured and recorded as the voltage is varied between the inner electrode in the solution and the outer electrode in the ionized gas surrounding the material being measured. As the voltage is varied from a positive voltage to a negative voltage, the current will vary from a negative value to a positive value. The zero current crossing will vary with a defect in the barrier.

Techniques using ionized gases are used to detect defects in protective barriers in accordance with one method of the invention. The conduction of electricity in gases has been considered since the time of Coulomb. The conductivity in a gas is derived from tearing loose electrons from neutral gas molecules to leave residual positively charged ions or liberating from solid or liquid surfaces near a gas positively or negatively charged particles. J.D. Cobine, *Gaseous Conductors* (1941); L.B. Loeb, *Basic Process of Gaseous Electronics* (1955). The energy needed for excitation or ionization may be given to an atom by impacts of electrons and positive ions. The absorption of a quantum of radiant energy or thermal collisions of neutral atoms in a hot gas also produce ionization of a gas. Ionization by electron collision depends on the energy of electrons. Slow and fast moving electrons are less effective in producing ion pairs than those with an optimum energy. A differential ionization coefficient, s, is defined in terms of the ion pairs produced by an electron traveling through a gas at a pressure of 1 mmHg as a function of the initial energy of the electron. A differential ionization coefficient varies with time due to energy losses from ionization collisions. Electrons with sufficient energy produce multiple ionization, so s is the sum of differential ionization coefficients for each order of ionization. When the electron energies are greater than 5000 volts, the number of electrons produced per molecule is for many gases such as air, $N_2$, $CO_2$, $NH_3$ on the order of about 14 to about 22. The differential ionization constant, s, is proportional to the gas density and number of atomic electrons per unit volume. Besides the above ionization processes which increase conductivity, other mechanisms can produce deionization of the gas through recombination and diffusion to decrease the electrical conductivity of the background medium.

The ion concentration at a given point in a container of ionized gases will depend upon the combined effects of ion generation, recombination, diffusion and mobility due to the electric field at the point. In addition to the electric field across the membrane the partial pressure outside the membrane produces a gradient.

The following equations are for two plates separated by a given distance so that a one-dimensional analysis is shown.

$$q_1 - an_1 n_2 + D_1 \frac{d^2 n_1}{d X_2^2} - \mu_1 \frac{d}{dx}(En_1) = 0 \qquad (I)$$

$$q_2 - an_1 n_2 + D_2 \frac{d^2 n_2}{d X_2^2} - \mu_2 \frac{d}{dx}(En_2) = 0 \qquad (II)$$

wherein, q is the ion generation/$cm^3$/second, assuming a steady state or uniform ions produced throughout the volume, $q_1$ - positive ion generation, $q_2$ - negative ion generation, recombination coefficient, $n_1$ - concentration of positive ions, $n_2$ - concentration of negative ions and electrons, $\mu_1$ - the mobility of the positive ions, $\mu_2$ - the mobility of the negative ions, $D_1$ - diffusion coefficient for positive ion, $D_2$ - diffusion coefficient for negative ion, where $dn/dt = q + D\nabla^2 n$.

Figure 2:
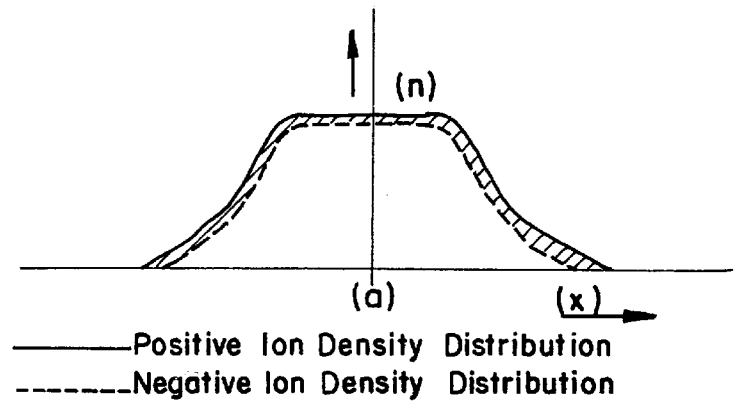
FIG. 2 is a graphical representation of ambipolar diffusion.
Figure 2:
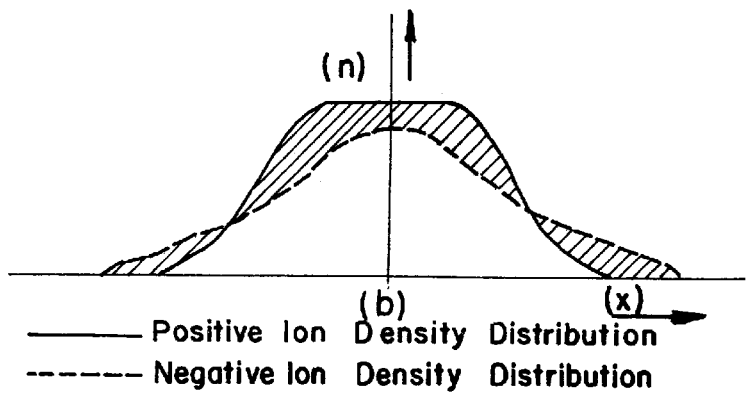
Figure 3:
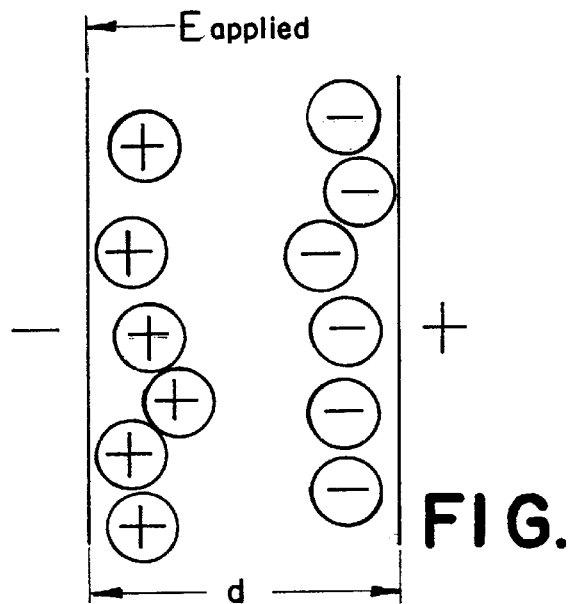
FIG. 3 is a schematic representation of the effect of electrical field E on the separation of ions over a distance d.

Since negative ions diffuse more rapidly than positive ions, a resultant positive charge is produced in a given region. The positive charge produced in a given region will tend to slow down the diffusion of the negative ions and speed up the diffusion of the positive ions due to the resultant field produced by the charges. Thus the effect of the differences in the diffusion coefficients of the positive and negative ions is to produce a partial electrical separation of the ionized gas as demonstrated in FIG. 2 which show ambipolar diffusion with the straight line representing positive ion density distribution and a broken line representing negative ion density distribution. FIG. 3 shows the effect of electrical field E on the separation of ions over a distance d.

If a sufficiently small defect is made in a protective barrier enclosure such as a glove, the equilibrium of the gas in the enclosure is distributed negligibly. The number of molecules emerging through the small defect is the same as the number of molecules which would strike the area occupied by the hole if it were closed off. The above technique known as effusion has been used to separate gas mixtures.

If the hole has a diameter D much smaller in size than the mean free path, L, of the molecules, there will be molecular effusion. However, if the molecules suffer frequent collision, which is so when D>>L, the gas will follow hydrodynamic flow. A typical gap at room temperature and one atmosphere pressure has a mean free path $L=10^{-5}$ cm. Even for a one micron hole, $D=10^{-4}$ cm, the diameter D is greater than the mean free path. A design with conductive gases at one atmosphere or less inside the glove should follow hydrodynamic flow.

In a partial vacuum, the mean free path L can be considerably longer than in one atmosphere. An ion, even though it has a massive particle size when compared to an electron, can have a sufficient velocity so that the gas particles through which it moves can be considered stationary. Therefore, the mean free path for such an ion, $L_i$, can be represented by the relationship $L_i=(\sqrt{2})(Lg)$ where Lg is the mean free path of the gas molecules. However, the presence of a gas does slow the motion of ions in an electric field because of repeated collisions changing the direction of the ion and the associated loss of energy.

Using the distribution of free paths as $n=Ne^{-x/2}$, where dN is the number of molecules having a free path of length between x and x+dx, and assuming a large number of collisions, the average drift velocity, $\bar{v}_d$, can be expressed as in equation (III) below, and the mobility, p, may be expressed as in equation (IV) below. The Langmuir equation for mobility of ions, where mass m and root mean square velocity, $V_{rms}$, moving through unionized gas particles of mass m is shown below in equation (V).

$$\bar{v}_d = \frac{Eq_i L}{m\bar{v}} \quad \text{(III)}$$

$$\mu = \frac{\bar{v}_d}{E} \quad \text{(IV)}$$

$$\mu = \frac{0.815 q_i \cdot L_i}{mV_{rms}} \quad \text{(V)}$$

At steady state, the average amount of energy of electrons and ions lost to gas particles at impact must be equal to the energy gained in an electric field. The resulting expression will be given in terms of the average kinetic energies of the electrons, positive and negative ions, particles, their masses and mean free paths, as well as the electric field intensity. Parameters such as variations in temperature, pressure, types of membrane, gas used, and intensity of electric field will be very important in determining the resultant steady states.

The velocity of the ions through a defect due to the pressure gradient across the defect in the membrane is determined by the following. Consider the mean force per unit area exerted on the wall by Newton's law equal to the mean rate of change of momentum of the wall. Consider equal partial pressures on each side of a barrier so there is a ΔP across the barrier producing the pressure gradient.

The pressure on the wall, $\bar{p}$, is expressed below in equation (VI) which simplifies to equation (VII), where $\frac{1}{6}(n)(\bar{v})$ is the mean number of collisions per unit time with the wall, F. Reif, *Fundamentals of Statistical and Thermal Physics* (1965), and $2m\bar{v}$ is the average momentum gained by the wall per collision.

$$\bar{p} = \frac{1}{A}(2m\bar{v})\left(\frac{1}{6}n\bar{v}A\right) \quad \text{(VI)}$$

$$\bar{p} = \frac{1}{3}nm\bar{v}^2 \quad \text{(VII)}$$

Across the defect in the membrane, assuming $\Delta p = p_1 - p_2$ where $p_1$ is the partial pressure at one side (1) and $p_2$ is the partial pressure at the other side (2), then the mean velocity coming through the defect is as expressed below in equation (VIII), where n is the number of particles and m is the mass of the gas particles or ions. This velocity $\bar{v}$ will add to the current density produced by the electric field reaction on the ions and electrons as expressed below in equation (IX).

$$\bar{v} = \sqrt{(3\Delta/mn)} \quad \text{(VIII)}$$

$$J = ne\left(\mu E - \frac{D}{n}\frac{dn}{dX} + \bar{v}\right) \quad \text{(IX)}$$

Thus, the current density and resulting equivalent conductivity is greatly enhanced by the pressure differential across the barrier membrane.

The invention will now be further described with respect to the following non-limiting example.

EXAMPLE 1

Figure 4:
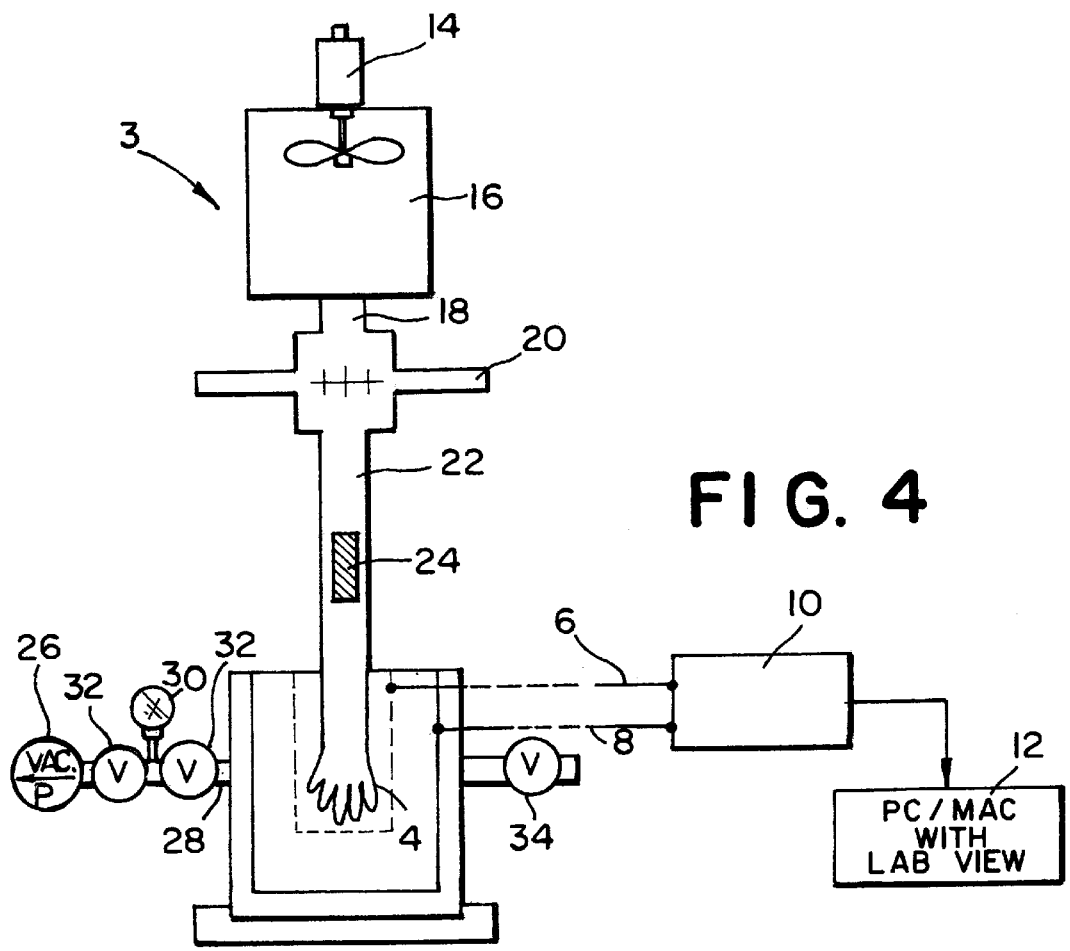
FIG. 4 is a schematic representation of a system for testing barrier materials in accordance with an embodiment of the invention with a portion of the apparatus broken away.

The schematic representation of this approach is shown in the apparatus 3 of FIG. 4 having the partial vacuum on the outside of a glove 4 and an ionized conductive gas inside the glove 4. Experiments were conducted based on the apparatus of FIG. 4 measuring defects for both latex and polymer gloves. The apparatus includes an inner screen 6 and an outer screen 8 attached across a Keithley electrometer 10 which is connected to a MacIntosh personal computer 12 with LabView® software. Gas is introduced at inlet 14 and passes through a fan 16. A blower or other means of flowing gas may be substituted for fan 16. The gas passes through an ionizer 18 in connection with a high voltage source 20 and RF generator 22 having an RF electrode 24 for capacitive coupling to form plasma. The ionizer 18 receives a high voltage which may be either of an AC current (60 Hz) or a DC current of a high voltage. A vacuum pump 26 in line 28 including a vacuum gauge 30 is provided having valves 32 on either side of gauge 30. The apparatus 3 is also equipped with a bleeder valve 34 for regulating partial pressure. While the apparatus 3 in FIG. 4 uses a high voltage ionizer 18 coupled with an RF source 22 as shown, it will be understood that either of the high voltage source or an RF source can be used independently within the scope of the invention.

A glove 4 is placed inside the conductive screen 6 in order to restrain the size of the glove expansion due to the partial vacuum. The size of the screens relative to the inflated glove size and strength of the glove is important, and the screens should be selected accordingly. For example, a latex examination glove placed in a 9 inch inner diameter screen would expand to fill the screen and keep its integrity until bursting around 30 kPa (about ⅓ atm) partial pressure. However, a screen of 13 inch inner diameter would allow the glove to expand to fill the screen and build a partial pressure of 10 kPa before bursting. The glove membrane becomes thinner as the glove expands. Thus, a large screen will cause the glove to burst at a much lower partial pressure due to thinning of the membrane as a result of glove expansion. Synthetic polymer gloves burst for given screen diameters at much lower partial pressures than due latex due to the different strengths of these materials.

The potential produced between two screens as a result of a line change and/or an electric field from a radiating source is determined from electromagnetic theory to be as set forth in equation (X) below. J.D. Kraus, *Electromagnetics* (1992).

$$(V_1 - V_2) = \Delta V = \frac{\lambda}{2\pi\varepsilon_o}\ln\frac{r_1}{r_2} \quad \text{(X)}$$

where $r_1$ and $r_2$ are as shown in FIG. 5 for concentric screens such as the screens 6, 8 in the apparatus of FIG. 4. Further, the radial component of the electrical field is as expressed below in equations (XI) and (XII).

$$E_r = \frac{\lambda}{2\pi\varepsilon_o} \quad \text{(XI)}$$

$$V = -\int_1^2 \frac{\lambda}{2\pi\varepsilon_o}dr \quad \text{(XII)}$$

wherein $\varepsilon_o$ is permittivity of free space r is radial distance where the electric field is measured λ is ionized charge, assumed to be uniform along the length of the screen cylinder=c/cm V is voltage.

As demonstrated with reference to FIG. 4, the ionizer 18 can radiate large electromagnetic fields which produce large ΔV's which mask the current density produced by the pressure gradient across a defect. Thus to reduce the ΔV to a value where the effects of Δp can be measured, the voltage to the ionizer 18 is preferably adjusted to just below the conditions for arcing. The electric field from the ionizer 18 produces a positive voltage on the outer screen 8 and a negative voltage on the inner screen 6. As the discharge produced by the ionizer 18 is blown into the glove 4 with no defects there is permeation through the glove 4 with electrons and possibly larger positive ions being controlled by the electric field between the cylindrical screens 6, 8. This produces for a given gas and barrier a background ΔV. A barrier with a defect will have the hydrodynamic term due to the pressure gradient across the defect producing first a negative ΔV jump from the surge of electrons flowing to the positive screen to produce a step decrease in the ΔV. The positive ions with a much smaller mobility than the electrons surge at a later time through the defect to produce an increase step in the ΔV above the background reading. If a derivative of the step increase is taken there is an impulse whose strength can be correlated with a hole size. The function from an electrometer can be fed directly to a LabView® program in a computer 12 such as a MacIntosh or any other suitable detector to monitor the impulse.

In order to increase the number of conductive ions and lower the pick up of the voltage radiated from the source to increase sensitivity, the partial pressure outside the glove 4 is greatly lowered. As shown in FIG. 6 in an alternative embodiment according to the invention, inside the glove and the ionizer 18 compartment a partial pressure is maintained by a control valve 36 and a vacuum pump 38 to control the ΔP for a safe pressure level as measured in kPa for a given glove. The partial pressure inside and outside the glove is adjusted for the desired ΔP. The decrease in the partial pressure inside the glove increases the mean free path and thus ion concentration inside the glove. A spectrometer such as QME 311 was used as a feedback to stabilize the background and indicate the permeability.

In order to establish a given background voltage difference, ΔV, for a given glove type, measurements are taken at a safe ΔP for the gloves using nitrogen ions or air. Nitrogen will ensure there will be not be ozone to deteriorate rubber latex although air can be used for polymers.

Also as shown in FIG. 6, another detection approach using conductive gases is to measure the current drawn between outer and the inner screens. This approach is similar to a vacuum tube configuration where the gaseous discharge replaces the cathode as a source of charges. A voltage is placed on the outer screen 8 which is greater in magnitude then that on the inner screen 6. The screen current through a 1 megaohm resistor 40 is measured by monitoring the voltage across it. The resistor is chosen to be large enough to present an impedance to the voltmeter and not to short out the screens. Even though the partial pressure between the screens is not the vacuum found in the vacuum tube, the analogy to a triode can be considered. The space charge in the region between the screens is fundamental in an analysis. B. Salzber et al., "Effects of Space Charge in Grid-Anode Region of vacuum Tubes," *Electron Tubes,* Vol. I., RCA Review, RCA Laboratories Division, Princeton, N.J.; B.J. Thompson, "Space-Current Flow in Vacuum Tube Structures," *Electron Tubes,* Vol. II, RCA Review, RCA Laboratories Division, Princeton, N.J. The polarity and magnitude of the applied screen voltages determine the operation of the configuration. Currents for various applied screens in the range of a few hundred volts produced currents in the nanoampere range. The ionizer operates at a voltage for negligible arcing, and partial pressure inside and outside of the barrier will increase ionization.

The increased ionization markedly increases the current density. This approach operating at a safe Δp will increase the sensitivity of this measurement.

In the above mentioned measurements the background output from a barrier with no pin hole defects is correlated with the steady state permeation rate and the breakthrough time. A quadruple mass spectrometer such as Balzers Quadruple mass Spectrometer QME 311 can be connected to the compartment surrounding the glove and or garment to monitor the permeation through a barrier in order to calibrate the above methods.

EXAMPLE 2

Figure 7:
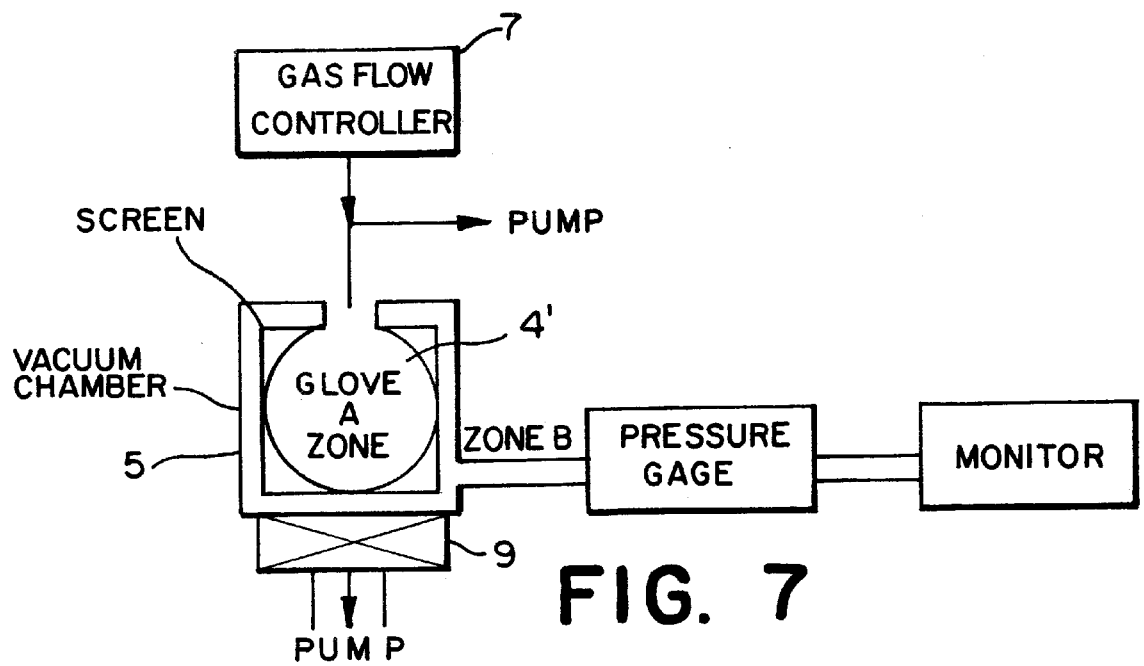
FIG. 7 is a schematic representation of a vacuum chamber for use in an embodiment of a method in accordance with the present invention.

A further embodiment is shown in the schematic system of FIG. 7 as used for testing and as described for use herein. A protective barrier 4' such as a surgical glove or surgical coat is attached to a holder mandrel and is inserted inside a vacuum chamber 5. The system is arranged such that a pressure difference of less than ΔP is maintained between the inside of the barrier (zone A) and its outside ambient zone B. The value of ΔP is dictated by the pressure difference needed to inflate the protective barrier 4' under investigation to fill the zone A. If this pressure difference exceeds a given value it will cause over stretching and final destruction of the barrier. In case of surgical gloves a pressure difference of about 0.1 atm. was needed to fully inflate the gloves to fill the given volume of zone A. The pressure inside zone A is kept constant by a balance of adjusting the pumping speed and gas flow. The pressure in zone B depends on the rate of gas leakage from zone A into zone B and the pumping speed of zone B. An ionization gauge can be used to measure with high degree of accuracy the pressure inside zone B. The ionization gauge works based on ionizing the gas by applying a high voltage between two electrodes. The generated current is measured and is related to pressure. From pressure and knowledge of the zone B pumping speed, the size of the hole can be measured in the barrier under investigation.

The vacuum system shown in FIG. 7 utilizes a flow controller 7 to control gas flow into zone A, a valve 9 for controlling the pumping speed, and a manometer for measuring pressure. A controller 7 will adjust the gas flow to achieve a background pressure for a constant pumping speed. By adjusting the pumping speed one can operate in a different range based on the leakage rate of zone A. It should be noted that the above arrangements have been used as standard practice in modem semiconductor processing, but have not been adopted for the use of applicants' invention as described herein.

Permeation can be determined by the background pressure of zone A. A measurement of the control gas flow will be an indication of the background pressure for gloves without defects but with permeation. Hazardous gas found in industry can be monitored for barriers on an inspection line permitting the evaluation of protection for a given barrier with a given hazardous gas.

The calibration for any of the above described systems and methods of the present invention may be undertaken for known hole sizes. The hole sizes of various sizes will be fabricated using the teachings of U.S. Pat. No. 5,286,432, incorporated herein by reference, wherein a glove membrane is stretched over a cactus needle held in a jig and hole cut with a micro electrode. The hole size will be verified and documented by using an Olympus PMG-3 microscope hooked in to a computer using NIH image software. Hole sizes in the microscope are fabricated, documented and tested. Graphs of outputs of the methods described above in Examples 1 and 2 for various hole sizes can be programmed for acceptance or rejection of barriers on an inspection line in accordance with standard computer programming methods. In a similar manner, background outputs of for the methods and systems as described above in Examples 1 and 2 for permeation rates of hazardous gas can be programmed for acceptance or rejection of barriers on an inspection line.

In the methods discussed in this disclosure, ionized gas with a pressure difference across a barrier measures defects by electrical detection. When there is no defect, the background voltage and/or current can be a measure of the permeability of the ionized gas. Although ionized nitrogen is normally used to detect defects, other hazardous chemicals can be ionized in the gaseous or plasma state and used to determine permeation with different ΔP's. This approach permits barrier defect measurements for hazardous chemicals on an inspection line. There can be marked differences in the challenges of gases, vapors and liquid to barriers as noted in J.O. Stull et al., *Am. Ind. Hyg. Assoc. J.*, 51 (5), pp. 291–296 (1990). However, presently used breakthrough times and permeation rates can be correlated with the ionized gas permeation for various gases and materials, permitting examination of each glove or garment on an inspection line. Correlation with a device such as a QME 311 spectrometer and the outputs of systems and methods as described above in Examples 1 and 2 can be used for the calibration for hazardous gas permeation through given barriers.

Another approach according to the present invention is the placing of a halogen or halogenated gas inside a barrier placed in a partial vacuum. The halogen gas will permeate through a defect into the partial vacuum where it is detected by a leak detector. An acceptable refrigerant gas such as 1,1,1,2-tetrafluoroethane is picked up by an electronic leak detector when it diffuses through a defect. Gases such as helium can be used and detected with a helium leak detector. The electronic detectors operate by ionizing the gas and monitoring the conductivity. These techniques require a constraining barrier as a screen adjusted to maintain the barrier integrity for a given ΔP. The above described techniques can be applied to an inspection line. A sequence of barriers are preferably be placed into screens of the proper dimensions in a controlled partial vacuum compartment. An ionized gas or gas plasma is fed into each barrier. Nitrogen from a nitrogen generator, or other suitable gas, can be ionized and used in the above operation, however, nitrogen is preferred as an inexpensive gas for measuring defects. It should also be understood, based on this disclosure, that some barriers may not need a constraining screen.

Hazardous gas could be used to monitor permeation using the above methods. A batch process which can process hundreds of gloves in one setting or an in-line vacuum load lock system can be used. In such methods, a glove or garment can be used, and a glove and/or garment tested one after another, individually. Both batch and load/lock methods for processing are known in the semiconductor industry and can be adapted for use in the present invention.

Figure 8:
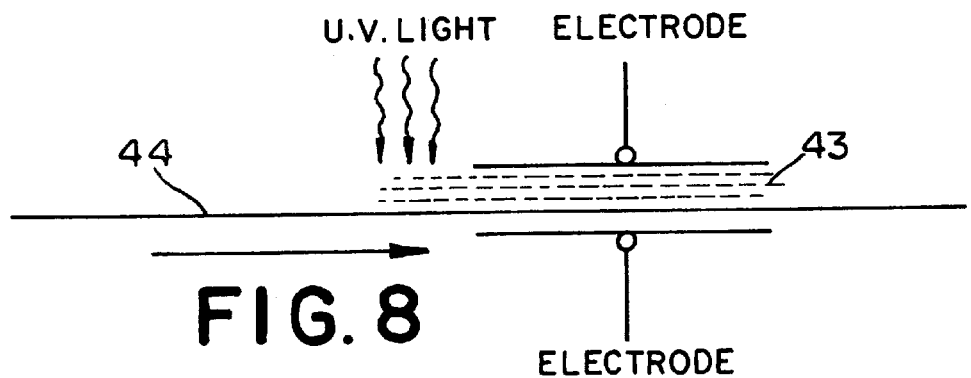
FIG. 8 is a schematic representation of use of conductive rollers in accordance with an embodiment of the method of the present invention.
Figure 9:
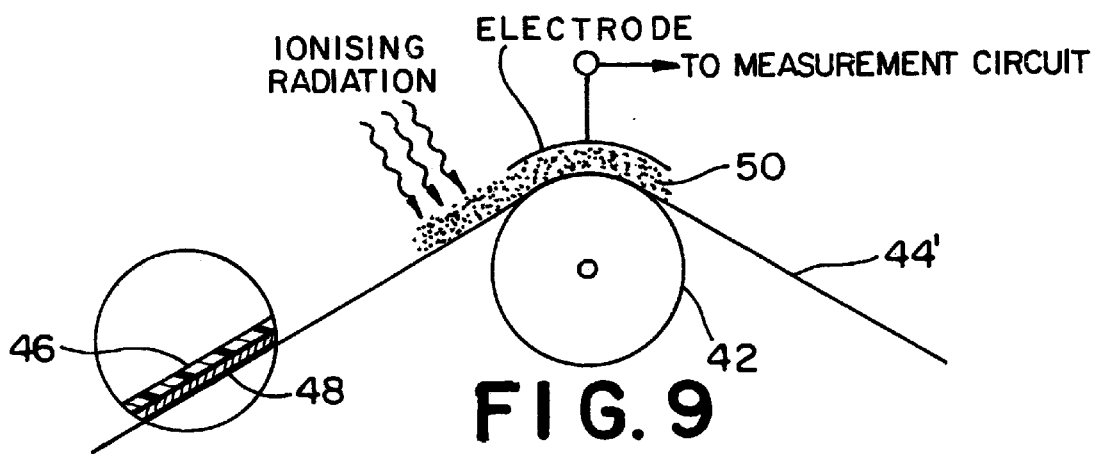
FIG. 9 is a schematic representation of the use of ionized media for measuring defects in accordance with a further embodiment of the present invention.

In a further embodiment in accordance with the present invention, for measurement of defects on food or medical packaging material, conductive rollers 42 can be used for electrical contact as illustrated with reference to FIG. 8. In some processes where the speed of the material being monitored or vibrations of the material in the production line prohibit the use of conductive rollers, a method for electrical contact without contacting the material being measured is needed. Examples of such a technique are the use of ionizing ultraviolet light or radioactive material or high voltage to ionize the air of a gas space above and/or below the measured material, are shown in FIG. 9. As shown in FIG. 9, ultraviolet light contacts the ionized medium 43 above sheet material 44 such as metal for use in food or medical packaging.

Figure 10:
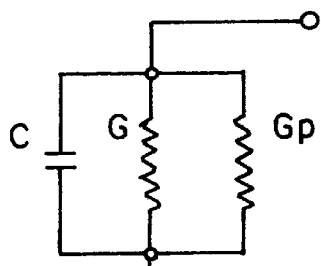
FIG. 10 is a schematic representation of the circuit in the embodiment shown in FIG. 8.

On the measurement of pin holes in sheet material 44' as shown in FIG. 9, either at rest or in motion on a production line various techniques and approaches described below utilize an ionized atmosphere to make a conductive path between a plate above and/or below the sheet 44' as shown in FIG. 9. The following detailed methods for the detection of defects such as holes through foil and plastic (dielectric) sheets are described below. With respect to FIG. 9, a conductive roller 42 is used in which the sheet 44' is made of non-conductive material such as plastic or other non-conductive material 46 with a layer of metal foil 48. However, the sheet may be made with or without a layer of metal foil on the sheet surface. The circuit which is formed as shown schematically in FIG. 10. With a sheet of non-conductive plastic side 46 on the roller 42 and the conductive foil 48 side facing the ionized medium 50, the pin holes which penetrate both foil and sheet can be detected.

If the sheet on the roller contains only non-conductive material such as the material 46, the pin holes on the sheet can be detected.

Figure 11:
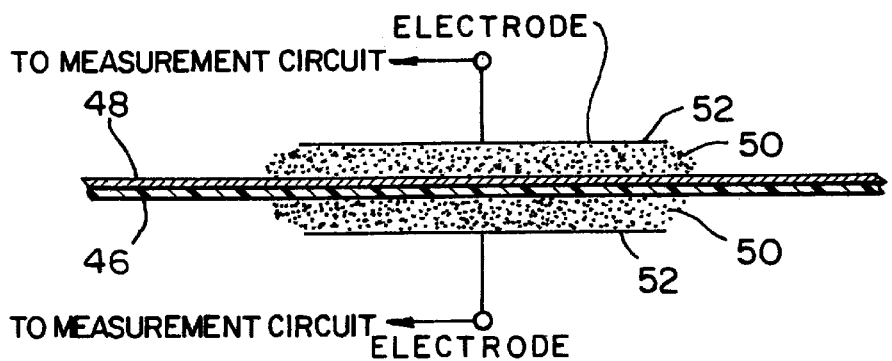
FIG. 11 is a schematic representation of another embodiment of the method of the invention using ionizing media on either side of a conductive foil and non-conductive sheet laminate and plate electrodes.
Figure 12:
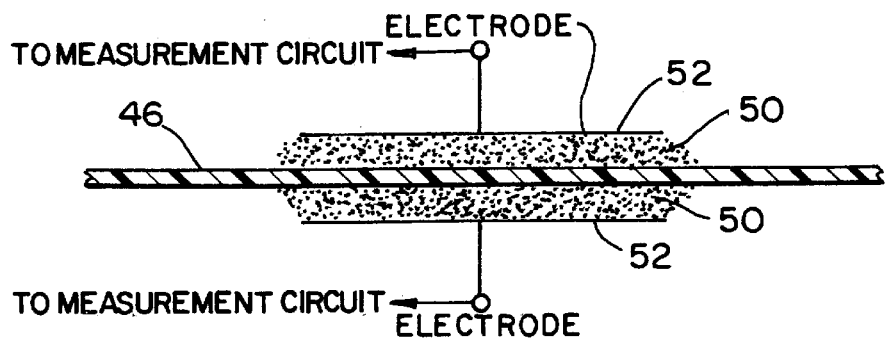
FIG. 12 is a schematic representation of another embodiment of the method of the invention using plate electrodes and a plastic sheet with ionizing media on either side of the sheet.

The invention may also be practiced using two plates with a moving or at rest sheet whose defects to be monitored are suspended between the electrodes with ionized medium above and below the sheet (detection of defects through foil and plastics) as shown in FIG. 11. In FIG. 11 the packaging sheet includes a plastic sheet 46 with metallic foil 48 as a coating, and ionized media 50 are used between the electrode plates 52 and sheet as shown in FIG. 11. As shown in FIG. 12, a plastic sheet 46 is tested using ionized media 50 above and below the sheet as shown and in between electrodes 52.

Figure 12A:
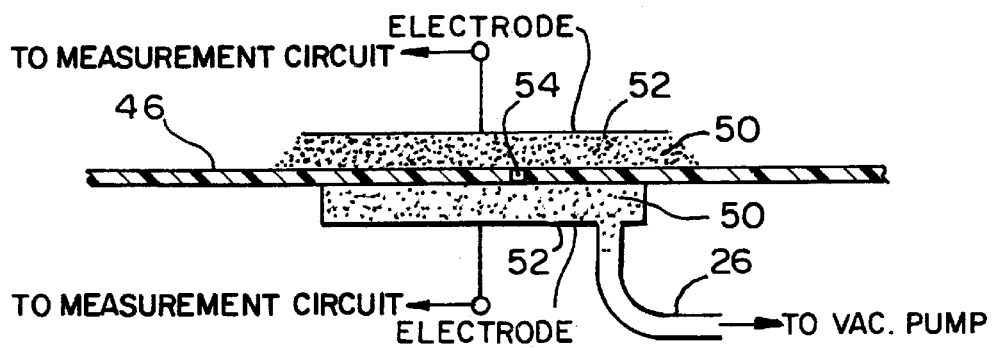
FIG. 12a is a schematic representation of an alternative embodiment of the method shown in FIG. 12 using a vacuum pump to increase pressure differential.

The use of a partial vacuum to increase the sensitivity of detection of pin holes or defects in barriers such as latex, plastic dielectric sheets, ceramic sheets, metal foils, thin metallic films and the like is demonstrated in FIG. 12a using the plastic sheet of FIG. 12 and connecting the system to a vacuum pump 26. A pinhole 54 in the sheet will permit ionized gases to be suctioned through the hole to create a short circuit to the electrode in the partial vacuum. This will greatly increase the conductivity to change the resonant circuit and/or other electrical impedance devices.

The above sheet arrangements could be used with a variety of impedance instrumentation besides a resonant Q meter circuit such as conductivity and impedance meters or any other suitable instrumentation providing a similar function. The ionized medium can be produced by using various sources of ionizing radiation including ultraviolet light, high voltage arcs (corona), radioactive (gamma) radiation, and other suitable forms of radiation above the sheet or in separate devices and blown across the sheet at the region of measurement.

In the above configurations with the ionized conductive medium, halogen, halogenated gases or helium gases can be used with a leakage detector to sense the leaking gas through a defect.

The monitoring of a surgeon's gloves, for example, in an operating room is a very important safety step to protect the surgeon's or other operating room personnel from defects in gloves used in the operating room. There are devices on the market which operate on a conductive electrode inside the glove to a conductive solution outside the glove. The sensing of defects is very similar to the techniques outlined in Beard, et. al., U.S. Pat. No. 5,196,799 issued Mar., 1993 for pin hole detection in protective barriers using conductive mandrel in a conductive bath to monitor electrical impedance, and or "Q" as an indicator of defects. However, the use of conductive baths in on operating room even with a bactericide has the potential for being hazardous.

Figure 13A:
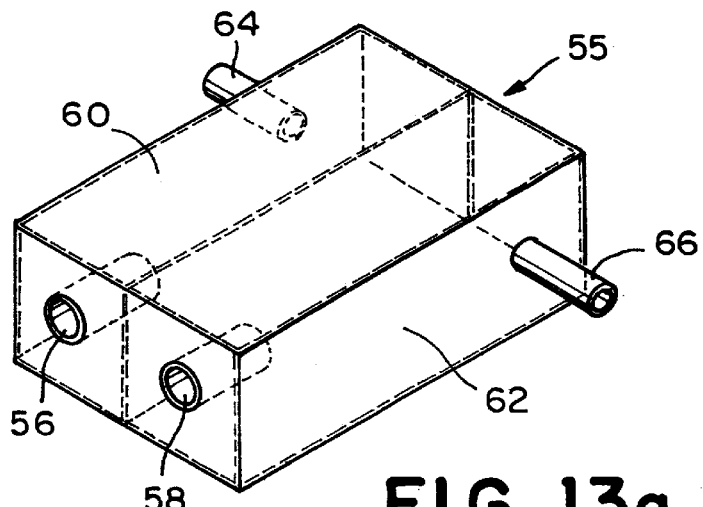
FIG. 13a is a perspective view of a two-chamber enclosure for testing surgical gloves in accordance with the invention.

In this disclosure the use of partial vacuum and gaseous conductors provides the advantages of ensuring a safer bacteria-free and virus-free sterile environment for testing gloves. An example of a preferred enclosure 55 for testing gloves for defects during an operation is shown in the below FIG. 13a. FIG. 13a shows left hand inlet 56 and right hand inlet 58 leading to respective chambers 60, 62. Both chambers are connected via lines 64, 66 to a vacuum source with a gauge. The side of the chambers 60, 62 opposite the inlets 56, 58 may be made of a translucent material for viewing the testing.

Figure 13C:
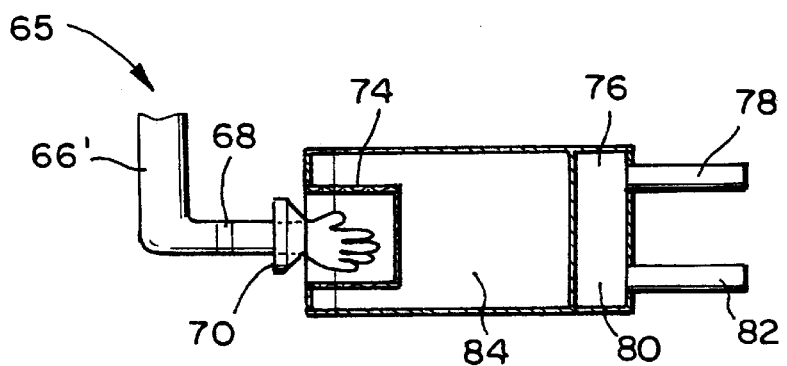
FIG. 13c is cross-sectional view of the interior a single chamber enclosure for testing gloves in accordance with an embodiment of the invention.
Figure 13B:
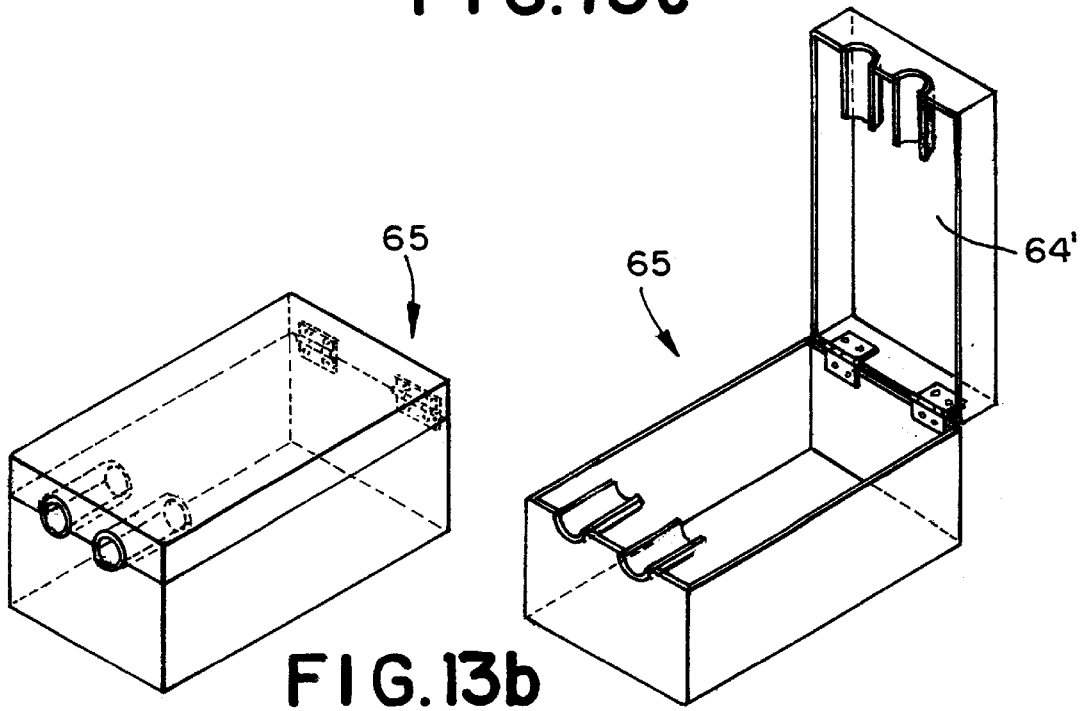
FIG. 13b is a perspective view of a single-chamber enclosure for testing surgical gloves having a hinged top in accordance with a further embodiment of the invention.

The container for left and right hand is preferably separate as shown in FIG. 13a, but need not be as shown in FIG. 13b which demonstrates an optional hinged top 64 for an alternative single chamber enclosure 65. The interior portion of the embodiment of a single chamber enclosure such as that of FIG. 13b is shown in FIG. 13c which includes an inlet 66 for introducing air, nitrogen, helium or other suitable gas an inflatable seal 68 for vacuum, and a metal-coated, such as a silver-coated plastic cuff 70 for receiving the glove or other barrier to be tested. The screen 74 may be made of aluminum or soft metal such that the glove may be expanded, but cannot be damaged from inside of the screen. An ultraviolet ionizer or other suitable ionizing source 76 is provided to the rear of the enclosure 65. Vacuum is drawn through outlet 78 in detector compartment 80 which is connected to detector and/or a high voltage ionizer at outlet 82. Partial vacuum is drawn in the interior portion 84 of the enclosure 65. If there is a large defect, the glove will not expand, blow out, and visible detection is sufficient. Inside of the glove can be air, nitrogen, helium and any other suitable gas. The gas will diffuse out of a small hole to be detected by an ionizer well away from the glove. The vacuum is preferably provided by a cryogenic or dry pump rather than an oil pump.

The present invention encompasses various barriers such as glove or condom barriers filled with conductive solution, such as saline for example, placed in a gaseous conductor medium with electrodes placed in the liquid and in the conductive gas. A programmable power supply may be applied to the electrodes so the voltage amplitude across the barrier is varied from a positive to a negative voltage or vice-versa. The zero crossing and/or slope of the voltage-current curve can be used to detect a defect and/or its size.

The invention further includes barrier materials such as glove and condom barriers having a conductive ionized gas and/or plasma on the outside and inside of the barrier as a means of detecting defects.

The use of a metallic and or conductive screens to constrain a protective barrier such as a glove or condom within a given volume when a partial vacuum is placed on one side of the barrier and a conductive gas on the other side is also within the scope of the invention as described above. The use of a second larger diameter screen to detect conductive gas permeating through a defect provides an advantageous conductive detecting means.

Monitoring of the voltage between two concentric cylindrical screens produced by the gaseous charge in the inside of the concentric cylindrical screen electrodes may also be used as a means of detecting defects in a barrier surrounding the inner screen.

Any suitable software, such as, preferably, the use of a LabView® program may be used to take the derivative of the voltage step function increase due to ions through the defect. The measurement of the strength of the resulting impulse voltage is used as an indication of hole size and existence of the defect in the barrier. The measurement of current from the screens surrounding such a barrier (glove) with a defect is also used as a measurement of the defect.

The invention further encompasses the treatment of the screens outside the protective barrier as in a vacuum tube configuration such as that of FIG. 6. Voltages are placed on the smaller inner and larger outer cylindrical screens. The voltages may be of different amplitudes and polarity as will be understood to those skilled in the art based on this disclosure. The space charge between the screens due to defects in the protective barrier are measured as in a triode by placing a sinusoidal signal on the inner screen and monitoring its amplitude value on the outer screen.

The sensitivity of the measurements in accordance with the invention, if needed, may be enhanced by connecting the screens to a vacuum tube or semiconductor (transistor device). The voltage difference generated by the ionic space charge due to defects may be used to bias the electronic devices in manners known to those skilled in the art.

The use of high voltage ionizers to produce ions is also within the scope of the invention, and may use conductive needle electrodes or sharp conductive bristles of brushes which form arcs or form glow discharges. The ionizing electrodes may also be arranged in symmetric geometries to enhance ionization.

Fans, blowers or any suitable means may be used to move the ionized gases into the barriers such as gloves and condoms.

R.F. energy coupled directly or capacitively into the gas to form a conductive plasma which is blown against the barrier may be used alone or in combination with ionizers.

The use of a partial pressure inside the barrier enhances the ionization of the gas. The adjustment of the voltage to the ionizer may be used to minimize arcing and thereby decrease the direct pick up voltage from the barrier.

The partial pressures on each side of the protective barrier may be controlled as described above to produce a ΔP across the barrier which will protect the integrity of the barrier in a given restraining cylindrical screen or other similar device with the proper diameter.

A sensor may be used in the compartment exterior to the glove to monitor the permeation through the barrier and or the flow of ionized gas through a defect. A Quadrupole Mass Spectrometer such as Blayzers Quadrupole Mass Spectrometer QME311 is preferred. Such a sensor inside the glove will preferably monitor radicals and ionization inside the barrier. The sensor may also be used to control the speed of one or more vacuum pumps to better control ΔP.

The combination of ionizing sources of a high voltage electrostatic ionizer and R.F. plasma as the conductive gas source is also within the scope of the invention as shown in FIG. 4 for example. The use of gases such as nitrogen and ammonia which form ionized radicals which are not detrimental to the barriers is preferred. The barriers may be latex synthetic polymers such as nitrile and composite materials. Air for some materials is acceptable while for others is detrimental because of ozone. This invention, however, is addressed to the selection of a gas with respect to the particular barrier to be used. Inert gases such as argon, xenon, etc., when ionized, can be used for otherwise sensitive materials.

Ionizing ultraviolet light radiation or radioactive radiation can also be used to produce ions when compatible with the barrier being used. The use of ionizing ultraviolet light radiation, radioactive radiation, or high voltage ionization and R.F. plasma to ionize the atmosphere between an electrode and any barrier geometry can be used to examine for defects.

The invention also include the specific measurements of defects in sheets using a device such as conductive rollers in contact with sheets, the use of ionized medium to create conductivity between electrodes and moving sheets, the application of partial vacuums to measure defects such as pin holes in metallic foils and/or sheets with plastic (dielectric) backup sheets as set forth above.

Various detecting means are also encompassed within the scope of the invention, including the use of resonant circuits, Q meter, conductivity, capacitance and impedance meters for detecting holes in sheet material.

Ions may be produced by radiation such as ultraviolet light, high voltage (corona-arcs), gamma radiation (radioactivity to enhance the electric conductivity above and/or below a sheet in order effectively to electrically place the detection electrodes on the sheet interface.

The invention includes the use of the various techniques described above for detecting pinholes and other leakage defects of ceramic substrates, glass, plastic, metal substrates such as those used in electric semiconductor circuits as well as other barriers noted above.

The use of a roller with perforations such as discrete holes or a porous conductive interface such as metals or conductive plastics may also be used to produce a partial vacuum under a plastic screen which is located between the barrier sheet and roller.

Halogen refrigerant gases such as 1,1,1,2-tetrafluoroethane can be used inside the barrier or over barrier sheets with a leak detector to detect defects. In addition, helium may be used with a helium leak detector to detect defects. The use of halogen gases and helium on one side of a barrier with a partial vacuum on the other side to increase the sensitivity of monitoring defects is also within the scope of the invention.

A partial vacuum compartment with ionizers placed to supply conductive media in the inside of the barriers so as to monitor the integrity of the barriers on an inspection line is a further embodiment of the invention as described above as well as the use of a partial vacuum with screen sizes designed to monitor the strength of various type barriers. For example, synthetic gloves form characteristic tears between the forefinger and thumb at much lower kPa partial pressures than viscsoelastic latex. Thus, such defects can be avoided by redesigning the gloves based on this aspect of the invention.

Larger constraining screens allow the barriers to expand until they burst at lower characteristic partial pressure due to thing of the barriers. Thus, the relationship between screen size and partial pressure before bursting can be used as a measure of barrier integrity as described above. The barrier integrity data may be used for improving the barriers to protect against unacceptable defects. As such, the application of the teachings of this disclosure may be used to ensure the integrity of protective garments worn in hazardous areas.

The background signal from screen enclosures surrounding a protective barrier without a defect may be monitored to measure the permeation of a hazardous gas through the barrier.

A conductive glove mandrel for fabricating the glove and detecting defects is also within the scope of the invention.

The mandrel may be dipped in a plastic solution or latex bath and the barrier vulcanized or dried before passing it through a compartment filled with a conductive gas. The conductive mandrel acting as one electrode and a screen electrode surrounding it are connected to a Q meter as described in U.S. Pat. No. 5,196,799 and other previously discussed detecting techniques of this patent.

Porous and/or screen mandrels can be used to support protective barriers. The protective barriers are placed over the supporting mandrels and a partial vacuum placed inside the mandrel with conductive gases placed outside the protective barrier. The resulting change in conductivity or potential between the outside screen electrode surrounding the protective barrier and an electrode inside the barrier with a partial vacuum can be used to monitor defects with detecting devices previously described or available from other sources.

Hole sizes in the micron range may be measured by adjustment of the inner screen to expand the barrier for increased hole sizes and thinning of the membrane of the barrier.

Food packaging with a conductive plastic or metallic material that is nontoxic and/or corrosive may be placed in the fluid inside the food package. The monitoring of changes in conductivity, Q, or potentials between this internal electrode and a surrounding electrode such as a screen can be used to detect defects. Outside the package can be an ionized gas and/or partial vacuum.

Packaged food placed in a compartment with a partial vacuum may also be tested. The packages may when needed be constrained in screen enclosure. A visual or electrical sensor can monitor the expansion of a package. A defective package remains collapsed (deflated).

A compartment which has a partial vacuum and a see-through window can be used to monitor defects and permeation. Medical packaging free of defects and containing medical implants are placed in the compartment. The package with implants will remain expanded due to the pressure difference between the outside and inside of the barrier of the package. A deflated package would demonstrate a defect. The implant package under suspicion would be checked for defects before using.

The pressurizing of encapsulating packages of medical implants with non-permeating sterilized gases can also be undertaken in accordance with the techniques of the invention. The visual deflation of the package during storage would indicate that the package must be tested for defects.

The placing of a small volume of pressurized gas in a viscoelastic impermeable barrier may be undertaken in accordance with the invention by using a small volume placed in the non-flexible and encapsulating package for medical implants. If the inside of the package is pressurized or at a partial vacuum, the small volume will change its volume with a defect in the implant package barrier. This change in volume of the small volume can be detected visibly or by a detector such as a light emitting diode whose light reflects off the small volume to a photo diode. Packaged implants are placed in a screen enclosure in a storage area under a partial vacuum. The packages expand to fill the screen enclosures. When there is a defect, a package will not fill the screen enclosure. A make or break in electrical contact between the package and screen can be used to signal with an audio and/or visual signal. Similarly, but using a storage area under pressure, the package volume may be is visually or electronically monitored for defects. A package with a defect will have much smaller volume.

Alternatively, the storage area may be at atmosphere pressure and the interior of the package enclosure is under pressure or a partial vacuum. The electrical contact or lack of contact between the enclosing package and surrounding screen can be used as a means of signaling a defect in the package.

The use of a barrier to separate two zones A and B as described above is also within the scope of the invention. The pressure in zone A is kept to a constant value by a balancing the pumping speed and gas flow into A. The pressure in zone B depends on the gas leakage by a defect or permeation into zone B and the pumping speed of zone B. A pressure gauge such as a manometer will monitor the pressure to determine if there is a defect and or permeation. In such as system, ionized nitrogen and or air can be used to monitor defects, and hazardous gases can be used to monitor the hazardous gases through barrier due to defects and permeation in specific barrier.

Using known hole sizes the pressure of zone B can be calibrated with the pumping speed to determine the size of a hole in a barrier under investigation. A measurement where the gas flow to a Zone A inside the barrier is adjusted for a given pressure in zone A. Gas leakage to zone B through micron holes will respond very fast while gas leakage due to permeation will be much slower. Thus two different pressure rises will be measured in zone B. The fast rise in pressure will be due to holes and the slow rise in pressure will be due a combination of the micron defect and permeation. Very hazardous gases can be diluted and the defects and permeation measured by the use of a quadrupole mass spectrometer and or sensing devices.

A batch probe with an enclosure of a large enough size to process two hundred gloves can be used. A partial vacuum in the enclosure surrounding the glove barrier is preferably controlled. The partial vacuum inside the gloves is also preferably controlled so the barriers fill an assembly of constraining screens to produce a given Δp across the barrier.

Ionizers inside the barriers can be used to produce ions and the calibrated voltages or currents used to evaluate the presence and size of defects. Background measurements are used to determine permeation rates. Hazardous gases can replace nitrogen to evaluate specific barriers for specific dangerous gases on a batch of gloves. Each glove or garment can be tested using an in line vacuum load lock system as used in the semiconductor industry and as noted above. The automatic moving of food packages on a conveyer into a compartment with a partial vacuum for batch monitoring of many packages is also within the scope of the invention.

The invention also includes use of RF coupling between the conductive top of an enclosure an a conductive bottom plate of the enclosure. A controlled partial vacuum in the enclosure expands in a controlled manner the volumes of the food packaging. The change in the reactance i.e. capacitance between the top and bottom plates due to a collapsed package with a defect can be monitored. The conductive plates can be segmented to permit localizing of a defective package.

The use of two enclosures as shown in the FIGS. 13a, b and c for the testing of the integrity of surgical gloves in an operating room is also within the scope of the invention. The wrist clamped so as to permit a vacuum in the enclosures to permit a partial vacuum. The two enclosures are connected to a monitored and controlled partial vacuum. The partial vacuum may be produced cryogenically dry pump or the less preferable oil pump. Air, nitrogen or helium is connected into the interior of the glove. The partial vacuum enclosure preferably has a leak detector to monitor the presence of any leakage of gas through a defect The detector may have high voltage electrodes for ionizing. At the end of the enclosure on intense ultraviolet source for ionizing gases such as air, which is monitored with conductive such as described above.

A single enclosure may be used, or can be designed in two halves as shown in FIGS. 13a, b, c with safety devices for clamping down on the two arms. The use of an alarm or visual read out is also preferred to indicate a defect or lack of integrity of the glove. The indicators of defects could be calibrated for hole size. The invention also encompasses use of such an application of the above glove detector to non surgical applications for detection of hazardous chemicals due to defects or permeation. The level when it becomes an unacceptable value would warn a worker to change the protective gloves.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. An apparatus for detecting defects in a barrier, comprising:
   (a) a barrier formed from a barrier material subjected to voltage from a voltage source across a first electrode and a second electrode;
   (b) an ionizer;
   (c) a gas inlet for introducing a gas to be ionized;
   (d) a vacuum source for drawing a gas to be ionized through an ionizer and through the barrier;
   (e) a controller for controlling a pressure differential across the barrier; and
   (f) a determination source for comparing electrical output for background permeation of ionized gas through the barrier material when the barrier material is free of defects with the output of ionized gas through the barrier.

2. The apparatus of claim 1, wherein the barrier material is a glove and the barrier material is selected from the group consisting of latex and plastic.

3. The apparatus of claim 1, further comprising an RF generator having a RF electrode.

4. The apparatus of claim 1, wherein the gas is selected from the group consisting of nitrogen, ammonia, helium, halogens, halogenated gases, and air.

5. The apparatus of claim 1, wherein the first and second electrodes are concentric.

6. The apparatus of claim 1, wherein the first and second electrodes are parallel plates.

7. The apparatus of claim 1, wherein the barrier material is a metal foil.

8. The apparatus of claim 7, wherein the foil further comprises a plastic sheet laminated to the foil.

9. The apparatus of claim 1, further comprising a fan or blower.

10. The apparatus of claim 9, wherein the fan or blower, the gas inlet, and the ionizer are enclosed within a vacuum chamber and the apparatus further comprises a second vacuum source for drawing vacuum in the vacuum chamber.

11. The apparatus according to claim 1, wherein a resistance is applied across the voltage source.

12. The apparatus according to claim 1, further comprising a gas flow controller, a pressure gauge and a monitor.

13. The apparatus according to claim 12, wherein said vacuum source is a vacuum pump and said apparatus further comprises an adjustable valve in communication with the vacuum pump.

14. A method for detecting defects in a barrier formed from a barrier material, comprising applying a voltage across a first electrode and a second electrode and across said barrier;

subjecting said barrier to an ionized gas, introduced from a gas inlet;

drawing the ionized gas through the barrier using a source for creating a pressure differential across the barrier;

measuring the voltage across the barrier when the ionized gas is drawn through the barrier; and comparing the voltage across the barrier to a voltage measured across a defect free barrier formed of the barrier material.

15. The method according to claim 14, wherein the gas is ionized by an ionization source selected from the group consisting of gamma radiation, ultraviolet radiation, and high voltage arcs.

16. The method according to claim 14, wherein the barrier is a foil laminate.

17. The method according to claim 16, wherein the foil passes across a conductive roller.

18. An enclosure apparatus for testing surgical gloves, comprising:

at least one chamber;

an inlet for introducing a surgical glove;

a gas inlet for passing gas through a surgical glove;

a screen for constraining the glove;

a vacuum source for drawing gas through a surgical glove;

an ionizing source; and a detector for monitoring voltage across a surgical glove within the screen.

19. The apparatus of claim 18, further comprising a seal on the inlet for introducing a surgical glove.

20. The apparatus of claim 18, further comprising a cuff for receiving a surgical glove at the inlet for introducing a surgical glove.

* * * * *